(12) United States Patent
Liu et al.

(10) Patent No.: US 8,831,891 B2
(45) Date of Patent: Sep. 9, 2014

(54) DIRECT SOLID SAMPLE ANALYTICAL TECHNOLOGY FOR DETERMINING A CONTENT AND A UNIFORMITY THEREOF IN A LYOPHILIZED KIT OF A SULFUR-CONTAINING CHELATOR WITH A STABLE COMPLEX CAPACITY FOR RADIOTECHNETIUM (TC-99M) AND RADIORHENIUM (RE-186, RE-188)

(75) Inventors: Kung-Tien Liu, Taoyuan County (TW); Ming-Yu Chao, Taoyuan County (TW); Yi-Chih Hsia, Taoyuan County (TW); Shih-Woei Yeh, Taoyuan County (TW); Mei-Hsiu Liao, Taoyuan County (TW); Lee-Chung Men, Taoyuan County (TW); Lie-Hang Shen, Taoyuan County (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 432 days.

(21) Appl. No.: 13/273,346

(22) Filed: Oct. 14, 2011

(65) Prior Publication Data
US 2012/0101741 A1    Apr. 26, 2012

(30) Foreign Application Priority Data
Oct. 21, 2010  (TW) .............................. 99135930 A

(51) Int. Cl.
*A61K 51/04*    (2006.01)

(52) U.S. Cl.
CPC .................................. *A61K 51/0478* (2013.01)
USPC .......................................................... 702/23

(58) Field of Classification Search
CPC .................................................. A61K 51/0478
USPC .......................................................... 702/23
See application file for complete search history.

(56) References Cited

U.S. PATENT DOCUMENTS

2009/0325311 A1*  12/2009  Lecerf et al. .................. 436/501

* cited by examiner

*Primary Examiner* — Bryan Bui
(74) *Attorney, Agent, or Firm* — WPAT, PC; Justin King

(57) ABSTRACT

The present invention is related to a direct solid sample analytical technology for determining a content and a uniformity thereof in a lyophilized kit of a sulfur-containing chelator with a stable complex capacity for radiotechnetium (Tc-99m) and radiorhenium (Re-186, Re-188). An economical, stable and easily accessible coal standard is used herein as a contrast substance to construct a sulfur calibration curve, followed by obtaining the sulfur content and the uniformity thereof in the solid lyophilized sample by interpolating the foregoing result into the sulfur calibration curve. Then, the weight content percent is converted to get the content and the uniformity of the chelator in the lyophilized kit. The quality control of active pharmaceutical ingredients (API) in the lyophilized kit during key production processes and clinical applications is thus assured.

8 Claims, 2 Drawing Sheets

DIRECT SOLID SAMPLE ANALYTICAL TECHNOLOGY FOR DETERMINING A CONTENT AND A UNIFORMITY THEREOF IN A LYOPHILIZED KIT OF A SULFUR-CONTAINING CHELATOR WITH A STABLE COMPLEX CAPACITY FOR RADIOTECHNETIUM (TC-99M) AND RADIORHENIUM (RE-186, RE-188)

CROSS REFERENCE TO RELATED APPLICATION

The application claims the benefits of the Taiwan Patent Application Serial Number 099135930, filed on Oct. 21, 2010, the subject matter of which is incorporated herein by reference.

BACKGROUND OF THE INVENTION

1. Field of the Invention

The present invention relates to a method for detecting a chelator content in a solid sample and, more particularly, to a direct solid sample analytical technology for determining a content and a uniformity thereof in a lyophilized kit of a sulfur-containing chelator with a stable complex capacity for radiotechnetium (Tc-99m) and radiorhenium (Re-186, Re-188)

2. Description of Related Art

As well known to those skilled in the art, a sulfur-containing chelator, which is a soft chelator widely applied to chelating radiotechnetium (Tc-99m) and radiorhenium (Re-186, Re-188), can complex stably with radiotechnetium and radiorhenium. Recently, a sulfur-containing radiopharmaceutical of radiotechnetium and radiorhenium comprises:

Tc-99m-ethyl cysteinate dimer (Tc-99m-ECD, a diagnostic drug for epilepsy), Tc-99m-mercaptoacetyltriglycine (Tc-99m-MAG3, a diagnostic drug for renal function), Tc-99m-dimercapto succinic acid (Tc-99m-DMSA, a diagnostic drug for renal cortex and pulmonary function), Tc-99m-N-NOET (a diagnostic drug for cardiac), Tc-99m-N-DBODC (a diagnostic drug for cardiac), Tropane derivatives (a contrast agent of dopamine transporters), Re-188 ECD/Lipiodol (a therapeutic drug of liver cancer) and an ethylenedicysteine-pharmaceutical adduct (capable of binding with various chelators and Tc-99m as disease constrasts) and the likes.

A general category of the sulfur-containing chelator, which can be complexed with radiotechnetium and radiorhenium, are shown in Table.1.

TABLE 1 a general category of the sulfur-containing chelator which can be complexed with radiotechnetium and radiorhenium.

| Coordinating nucleus of radiotechnetium and radiorhenium | chelator | chelating structure |
|---|---|---|
| Penta- and Hexacoordinated complexes of oxo-Tc or oxo-Re ([M=O]$^{3+}$) | Thiolates | S |
| | Aminothiolates |  |
| | Dithiolates or dithioxalates |  |
| | Tridentate dithiolates |  |
| | |  |
| | |  |
| | Tridentate Schiff bases |  |
| | Diaminedithiolates |  |
| | Mercaptoacetamides |  |
| | MAG3 derivatives |  |
| | Thioalkyl-dithiol-thio |  |
| Penta- and Hexacoordinated complexes of nitrido-Tc or nitrido-Re ([M≡N]$^{2+}$) | Thiourea | S |
| | Dithiocarbamate |  |
| | Azomethines |  |
| | Diaminedithiolates |  |
| | Isothiocyanate | RN=C=S |

As clinical use, a lyophilized kit comprising a chelator and a reductant is usually dissolved in a buffer solution, and then the chelating reaction (also known as complex reaction or radiolabeled reaction) is preceded by mixing radiotechnetium or radiorhenium. After producing a complex, a patient's intravenouse injection is performed.

Traditionally, most methods for measuring a content of a sulfur-containing chelator in a lyophilized kit are dissolving the sample, titrating then instrumental analyzing.

A first conventional method for measuring sulfur in liquid samples refers to Eschka method. The method is a standard method of the total sulfur content such as organic sulfur, inorganic sulfur and elemental sulfur, which is adopted by ISO and ASTM. However, the chemical pretreatment process of the method is too complicated and mainly applied to the measurement of the total sulfur content in coal, oil coke, and/or coke, and thereby the method is inappropriate for analyzing organic sulfur-containing chelators.

A second conventional method for measuring sulfur in liquid samples refers to using inductively coupled plasma atomic emission spectrometry (ICP-AES) and potentiometric to analyze sulfur content. The disadvantage of the method as described above is that the method is only used to analyze liquid samples, and thus many complicated chemical pretreatment processes before analyzing, including steps of decomposing, dissolving, purifying and the like, are a must. Because of rapid degradation after dissolving parts of the sulfur-containing chelator in the lyophilized kit such as ECD Vail A, some problems such as sample loss and contamination or the like, may be caused during processing. Accordingly, using instruments after dissolving samples such as high performance liquid chromatography (HPLC) or mass spectrometric analysis is not suitable for analyzing such samples. Further, the analytic method of the sulfur content is also related to the sulfur chemical conformation. For example, a third conventional method for measuring sulfur in liquid samples refers to Canfield et al. research, which a reduction method of chromium is used to analyze inorganic sulfur in sediments, shales and argillites, comprising pyrite elemental sulfur and volatile monosulfide. Nevertheless, the reduction method only has a higher specificity for reducing inorganic sulfur rather than reduces organic sulfur and sulfates, and thus fails to completely determine the real sulfur content of organic compounds.

Disadvantages for analyzing liquid samples may be known as described above, therefore, if solid samples may be directly analyzed, an analyte loss during dissolving samples may be avoided. Further, there may be many merits according to the undiluted samples, such as the increased analytic sensitivity, the decreased amount of requiring samples, the no requirement of corrosive and hazardous reagents, the frugal expenditure, the environmental protection and the faster analyzing rates. However, there are still some defects to directly analyze solid samples, including a difficult sample operation, especially during the process wherein samples are introduced into instruments, an arduous standard calibration due to the process of gasification and an analyte atomization which is related to forms and substrates of the analyte in solid samples, an unsatisfactory precision such as a range of 5~25% of a relative standard deviation (RSD) for analyzing solid samples by solid sampling-graphite furnace atomic absorption spectrometry (SS-GFAAS) and Solid Sampling-Electrothermal Vaporization-Inductively Coupled Plasma-Mass Spectrometry (SS-ETV-ICP-MS), and other problems induced by introducing other substrates into instruments while directly analyzing. Additionally, the direct analysis of solid sample has a common range of 10~20% of a relative standard deviation.

A first conventional method for measuring sulfur in solid samples refers to X-ray fluorescence spectroscopy, which is developed by Nečemer et al for directly analyzing the sulfur content of solid powders in feed. However, the pattern resolution of the baseline separation may not be obtained by such a method, and thus quantitative analysis software is developed by them. Besides, a comprehensive standard uncertainty and an accuracy of such method are 12% and 2~10% respectively, and the main error of such method derives from sampling uniformity of solid samples.

A second conventional method for measuring sulfur in solid samples refers to instrumental neutron activation analysis (INAA) which is developed by Nečemer et al for directly analyzing the sulfur content of solid powders in feed. However, related equipments for neutron irradiating and radiation protecting are necessary for INAA, and 3000-5000 mg/kg of a lower detecting limit is unsatisfactory.

A third conventional method for measuring sulfur in solid samples refers to using an elemental analyzer. For example, a method which an elemental analyzer coupled with an isotope ratio mass spectrometer (Sieper et al.) was developed to simultaneously analyze the isotope ratio of elements including hydrogen, carbon, sulfur and nitrogen within twenty minutes. Besides, Carlo Erba elemental analyzer (Duz et al.) was applied to hydrogen, carbon, sulfur and nitrogen analysis in coal samples. Although using the elemental analyzer for solid samples has been known to Pharmaceutical industries and applied element content analysis to a single pharmaceutical, the method described above has never been used to directly analyze the content and uniformity thereof in the lyophilized kit of the sulfur-containing chelator with a stable complex capacity for radiotechnetium (Tc-99m) and radiorhenium (Re-186, Re-188) until now.

Above all, a technology for directly analyzing solid samples is immediately needed, which may be easily operated, provided with high precision and applied for determining the content in the lyophilized kit of the sulfur-containing chelator with a stable complex capacity for radiotechnetium (Tc-99m) and radiorhenium (Re-186, Re-188), and thereby problems due to prior arts may be resolved.

SUMMARY OF THE INVENTION

Determining a content and a uniformity thereof of chelator active ingredients in a lyophilized kit is a significant test item for maintaining chemical, manufacturing and control qualities. An aspect of the present invention is related to a direct solid sample analytical technology for determining a content and a uniformity thereof in a lyophilized kit of a sulfur-containing chelator with a stable complex capacity for radiotechnetium (Tc-99m) and radiorhenium (Re-186, Re-188), and thus the pharmaceutical quality of the lyophilized kit during mass production may be assured by the method.

In one embodiment, a method for directly analyzing solid samples is provided, which may be easily operated, provided with high precision and applied for determining a content and a uniformity thereof of active ingredients of a sulfur-containing chelator in a lyophilized kit, comprising:

a sample-preparing step, which comprises a contrast substance preparing process and a lyophilized testing substance preparing process, wherein the contrast substance preparing process comprises: preparing a contrast substance, a run-in sample, a calibration curve standard and a quality control sample, while the lyophilized testing substance preparing process comprises: preparing a kit blank of the lyophilized testing substance and a sample, wherein the sample is related to the sulfur-containing chelator;

An analyzing step using an elemental analyzing equipment, wherein the elemental analyzing equipment is used for the following substeps, comprising: a system suitability test, a substrate background analysis for the kit blank of the lyophilized testing substance, a contrast substance analysis, a quality control sample analysis and a sample analysis, wherein the system suitability test comprises: a system background test and a run-in sample test;

A calculating step for a content of a contrast substance and a quality control sample, which comprises: a calculating substep for a linear regression formula and a correlation coefficient of the contrast substance and a calculating substep for an accuracy and a recovery yield of the quality control sample, wherein the calculating substep for the linear regression formula and the correlation coefficient of the contrast substance comprises: calculating a sulfur content of the contrast substance, preparing a calibration curve, and calculating the linear regression formula and correlation coefficients, while the calculating substep for an accuracy and a recovery yield of the quality control sample comprises: calculating a theoretical value and an experimental value for the sulfur content of the quality control sample and the recovery yield thereof; and A converting substep for calculating a sulfur content of a sample into a content of a sulfur-containing chelator, wherein comprises: calculating the sulfur content in a testing substance and calculating a chelator content in the testing substance.

In one embodiment, the elemental analyzing equipment is the elemental analyzing equipment, which coupled with a non-dispersive infrared detector, a thermal conductivity detector or a mass spectrometer or the like. In a specific embodiment, the mass spectrometer as described above may be, but limited to an isotope ratio mass spectrometer, an inductively coupled plasma mass spectrometry, a gas chromatograph mass spectrometry, a liquid chromatography mass spectrophotometer or a tandem mass spectrometry.

In one embodiment, the sulfur-containing chelator may be a precursor of the sulfur-containing chelator, which has a stable complex capacity for radiotechnetium (Tc-99m) and radiorhenium (Re-186, Re-188). In some embodiments, the precursor disclosed herein may be applied to diagnostic or therapeutic radiopharmaceuticals after chelating with radiotechnetium and radiorhenium. In other embodiments, the sulfur-containing chelator further comprises, but is not limited to: thiolates, aminothiolates, dithiolates, dithioxalates, tridentate dithiolates, tridentate schiff bases, diaminedithiolates, mercaptoacetamides, mercaptoacetyltriglycine (mag3) derivatives, thioalkyl-dithiol-thio, thiourea, dithiocarbamate, azomethines, diaminedithiols or isothiocyanate.

In one embodiment, the contrast substance is a sulfur-containing compound or a sulfur-containing mixture. For example, the sulfur-containing compound may comprise but not limit to sulfanilic acid or 4-aminobenzene sulfonic acid, while the sulfur-containing mixture may comprises but not limit to coal.

Other objects, advantages, and novel features of the invention will become more apparent from the following detailed description when taken in conjunction with the accompanying drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings, FIG. 1 (FIGS. 1A and 1B) illustrates a diagram showing a direct solid sample analytical method for determining a content and uniformity thereof in a lyophilized kit of a sulfur-containing chelator with a stable complex capacity for radiotechnetium (Tc-99m) and radiorhenium (Re-186, Re-188).

DETAILED DESCRIPTION OF THE PREFERRED EMBODIMENT

Figure 1A:
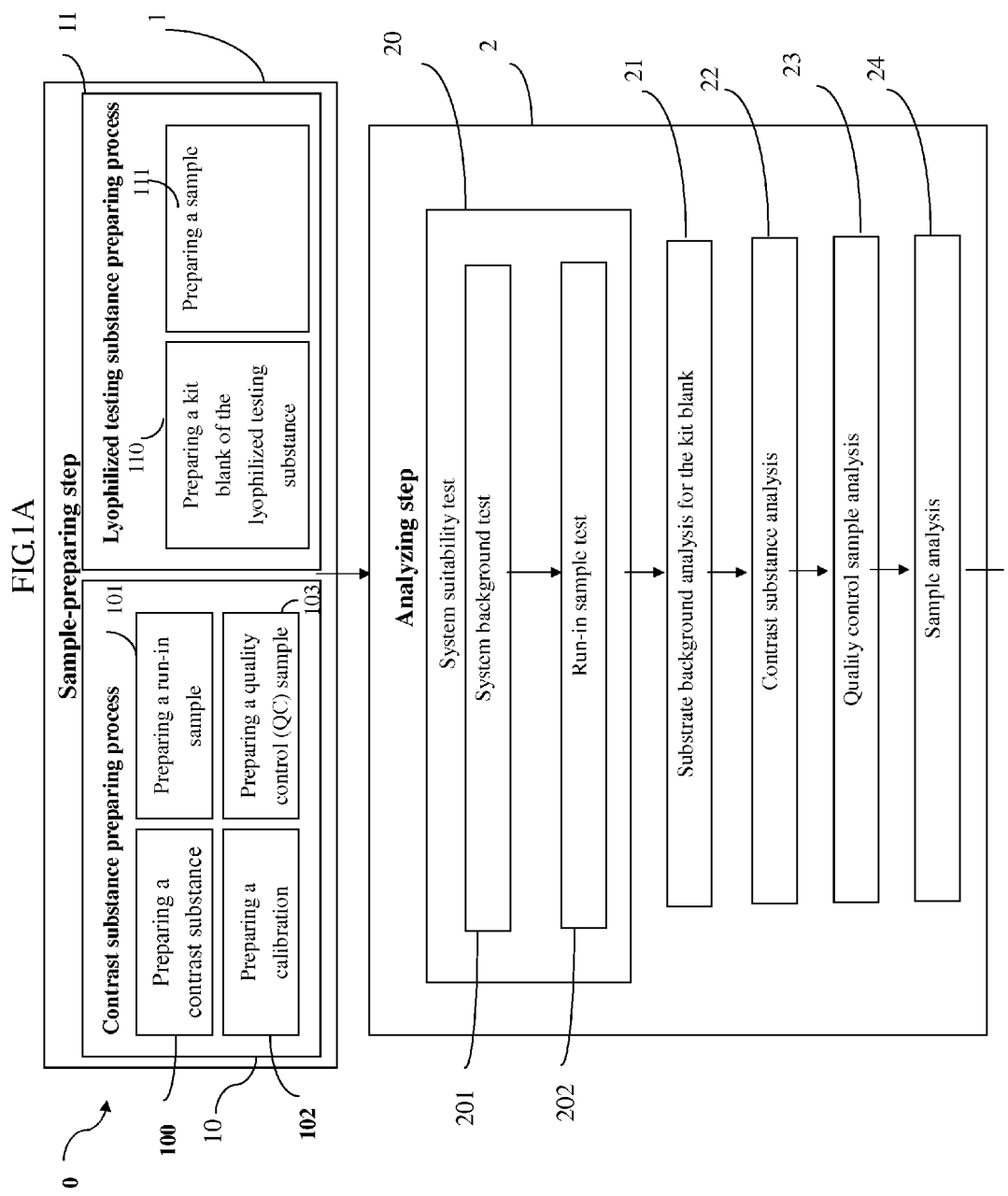

The above and other objects, features and advantages of the present invention will be more clearly understood from the following detailed description taken in conjunction with the accompanying drawings, in which:

A direct solid sample analytical method is provided in the present invention, which is used for determining the content and the uniformity thereof in the lyophilized kit of the sulfur-containing chelator with the stable complex capacity for radiotechnetium (Tc-99m) and radiorhenium (Re-186, Re-188). The sulfur content of solid samples in the lyophilized kit is expected to be analyzed directly, there follows a conversion of the sulfur content into a chelator content according to the chelator which is the only sulfur-containing ingredient in the formula of the lyophilized kit. Thus, there is no need to analyze after dissolving samples to avoid some problems such as the instability or the degradation caused by dissolving solid samples of the lyophilized kit.

As used herein a sulfur-containing chelator has a stable complex capacity for radiotechnetium (Tc-99m) and radiorhenium (Re-186, Re-188), which can be applied to a precursor (i.e. active pharmaceutical ingredient, API) of the sulfur-containing chelator in diagnostic or therapeutic radiopharmaceuticals. As used herein a "lyophilized kit" of a sulfur-containing chelator refers to a reagent produced by premixing the sulfur-containing chelator with reductants such as $SnCl_2$ or the like, and then lyophilizing the mixture. Thereby, the lyophilized kit can be used to facilitate mass production, transportation and clinical use.

Using an elemental analyzer (EA) disclosed herein refers to a method, which analyzes solid samples directly for determining the content and the uniformity thereof in the lyophilized kit of the sulfur-containing chelator with the stable complex capacity for radiotechnetium (Tc-99m) and radiorhenium (Re-186, Re-188). Although the EA has been fully mature to widely applied in chemical constitution analysis of pure compounds, such a method has never been applied in general solid sample analysis of the content and the uniformity thereof in the lyophilized formula of the sulfur-containing chelator, especially for analyzing the sulfur-containing chelator which has a "soft" stable capacity for radiotechnetium (Tc-99m) and radiorhenium (Re-186, Re-188). The EA coupled with a non-dispersive infrared detector (NDIR), the EA coupled with a thermal conductivity detector, or the EA coupled with an isotope ratio mass spectrometer may be used as analytic tools in the present invention.

Examples 1

The Substrate Effect Test of Coal

Because the calibration curve of the lyophilized kit of sulfur-containing chelator was inaccessible, the calibration curve could be constructed by a contrast substance instead, wherein the contrast substance could be, but not limited to a sulfur-containing compound or a sulfur-containing mixture. The sulfur-containing compound could comprise, but not limited to sulfanilic acid, 4-aminobenzene sulfonic acid and the like. In one embodiment, the contrast substance referred to a coal standard, wherein the model number thereof is ELTRA coal standard #92510-50, the constitution comprises 76.6% of the carbon and 3.07% of the sulfur, and the commercial source is ELTRA, Neuss, Germany. The advantages using coal as the contrast substance were that: easily access, standard value with sulfur content, low cost, better stability, good preservation and no question of the coal substrate interference after experimenting.

Referring to table.2, the coal substrate effect test was shown that the sulfur content was directly measured in coal or measured by putting coal into the lyophilized kit without any chelator. Coal was not interfered with the substrate according to table. 2.

TABLE 2 the Substrate Effect Test Of Coal

| Sample | Sulfur content (mg) | The formula of linear regression | Correlation coefficient (r) | Peak area |
|---|---|---|---|---|
| Coal | 0.033~0.142 | $Y = 1.565 \times 10^{-6}X + 3.174 \times 10^{-3}$ | 1.0000 | 248 ± 11 |
| Coal which puts into the lyophilized kit without any chelator | 0.036~0.132 | $Y = 1.547 \times 10^{-6}X + 8.932 \times 10^{-3}$ | 0.9998 | 2438 ± 642 |

2. Optimal Parameters of the Sulfur Content of ECD.2HCl Analysis by IR-EA

Then, a sample pretreatment process of a coal contrast was amended by ASTM method D-3173, 2002. Further, analyzing instrument parameters of partial sulfur-containing chelator by the EA was amended by the method developed by Sieper et al., wherein elements such as hydrogen, carbon, sulfur and nitrogen were simultaneously analyzed by the EA coupled to the isotope ratio mass spectrometer.

The embodiment disclosed herein illustrated examples, but was not limited to content analysis of ECD.2HCl, which was a major ingredient in a kit A of a lyophilized injection for a brain imaging agent of ethyl cysteinate dimer. In the embodiment, the instrument could be, but not limited to the EA coupled with a NDIR (hereinafter called the IR-EA), wherein the model number thereof was vario EL cube, while the commercial source was Elementar Analysensyteme GmbH, Hanau, Germany. Parameters of the instrument (see Table.3) was shown that the optimal Parameters of the sulfur content of ECD.2HCl analysis by IR-EA. If different instruments were used, those instruments could adjust parameters.

TABLE 3

Optimal Parameters Of The Sulfur Content
Of ECD•2HCl Analysis By IR-EA

| Analyzing mode | CHNS |
|---|---|
| Combustion tube temperature (° C.) | 1150 |
| Reduction tube temperature (° C.) | 900 |

TABLE 3-continued

Optimal Parameters Of The Sulfur Content
Of ECD•2HCl Analysis By IR-EA

| Analyzing mode | CHNS |
|---|---|
| Injection gas/time (sec) | He/10 |
| Injection time of $O_2$ | 120 |
| Waiting temperature of $CO_2$ (° C.) | Environment temperature |
| Waiting temperature of $H_2O$ | Environment temperature |
| Waiting temperature of $SO_2$ (° C.) | 140 |
| desorption temperature of $CO_2$ (° C.) | 240 |
| desorption temperature of $H_2O$ (° C.) | 150 |
| desorption temperature of $SO_2$ (° C.) | 220 |
| Carrying gas/flow rate (ml/min) | He/230 |
| Flow rate of $O_2$ | 15 |
| Flow rate of $O_2$ during combustion | 30-35 |

3. Analytic Procedure

Figure 1B:
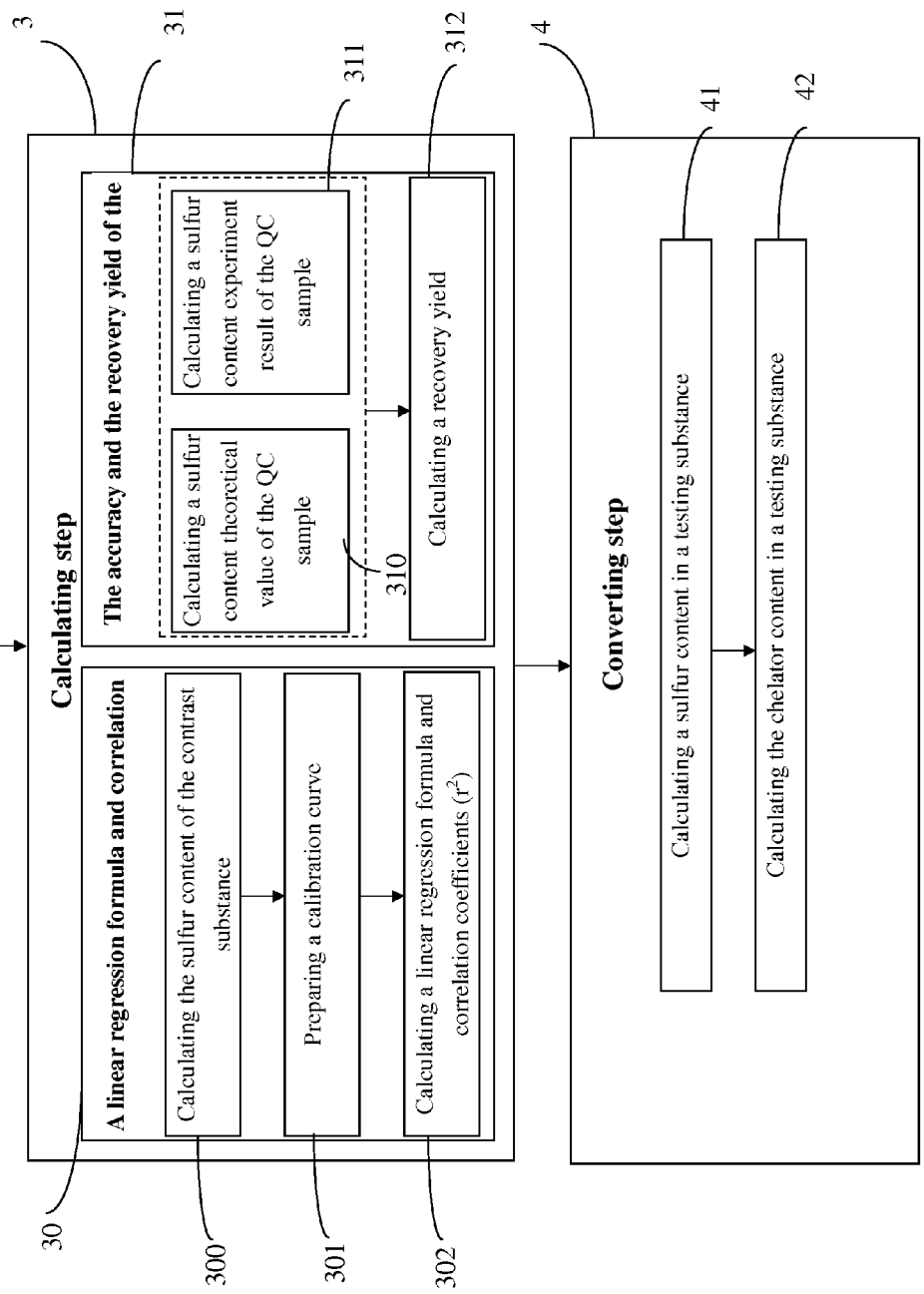

A diagram (see FIGS. 1A and 1B) was shown that the direct solid sample analytical method disclosed herein for determining the content and the uniformity thereof in the lyophilized kit of the sulfur-containing chelator with the stable complex capacity for radiotechnetium (Tc-99m) and radiorhenium (Re-186, Re-188). The direct solid sample analytical method described above comprised: a sample-preparing step 1, a analyzing step 2 using an elemental analyzing equipment, a calculating step 3 for the content of the contrast substance and the quality control sample, and a converting step 4 for calculating the sulfur content of a sample into the content of a sulfur-containing chelator.

3.1 The Sample Preparing Step

First, the sample-preparing step 1 further comprised a contrast substance preparing process 10 and a lyophilized testing substance preparing process 11, wherein the process 10 could be optionally before the process 11, or vice versa.

The contrast substance preparing process 10 further comprised a substep 100 for preparing a contrast substance (i.e. a coal standard). In certain embodiment, about 0.5 g of the coal standard were grinded with an agate mortar about 1 to 2 minutes, then put into a backing oven under 107° C. to bake about 90 to 120 minutes. Next, the coal standard was taken out, cooled in a drying oven to the room temperature and ready for use.

Preparing a run-in sample referred to a substep 101, in which the coal standard as described above exactly weighed 2±0.2 mg as a run-in sample.

Then, the analyzed run-in sample was tested and confirmed after covered with a tin box specific to an elemental analyzer (hereinafter called a EA tin box).

Preparing a calibration curve standard referred to a substep 102, in which five coal standards as described above exactly weighed that had a weight selected from the range of 1 to 3.5 mg and then those coal standards were covered with the EA tin box.

Preparing a quality control (QC) sample referred to a substep 103, in which foregoing coal standards weighed exactly 2±0.2 mg as QC samples and those coal standards was covered with the EA tin box. Then, the number of QC samples could be at least 20% of a total of samples per batch, wherein the number could be at least 3 with the proviso that the number be a multiple of 3. Sequence of substep 100 to 103 could be changed optionally up to the operator.

The lyophilized testing substance preparing process 11 further comprised a substep 110 for preparing a kit blank of the lyophilized testing substance (hereinafter called Kit Blank). A proper amount of a Kit Blank was grinded with the agate mortar about 40 seconds. Two Kit Blanks weighed exactly about 7.5 mg and were covered with the EA tin box.

A substep 111 was referred to preparing a sample, which comprises a sulfur-containing chelator. In a specific embodiment, the sample disclosed herein referred to ECD Vail A which was taken to grind with the agate mortar about 40 seconds. About 7.5 mg of samples were weighed exactly and covered with the EA tin box.

3.2 The Analyzing Step

Then, the analyzing step 2 proceeded, wherein the EA equipment was used for analyzing and following substeps, further comprising a substep 20 of the system suitability test, a substep 21 of the substrate background analysis for the Kit Blank, a substep 22 of the contrast substance analysis, a substep 23 of the quality control sample analysis and a substep 24 of the sample analysis.

The substep 20 referred to a system suitability test, which should be performed before every analysis test, while the contrast substance and the testing substance could be analyzed after up to the standard. The system suitability test further comprised a substep 201 referred to a system background test and a substep 202 referred to a run-in sample test.

In certain embodiment, at least six blank tin boxes without any samples were analyzed in the substep 201 until the background was stable. Finally, several blank tin boxes were analyzed the background, calculating the integral area of the sulfur average background. The acceptable standard of the system background had less than 5000 counts of the sulfur background of several blank tin boxes (i.e. the integral area).

In certain embodiment, the integral area of the sulfur average background was calculated by three samples of blank tin boxes. In certain embodiment, sulfur content of 8 to 12 coal run-in samples was analyzed in the substep 201 to confirm the instrumental reproducibility. Finally, the relative standard deviation (RSD) of the sulfur content ratio was analyzed and calculated by coal run-in samples. In certain embodiment, the number of analyzed and calculated coal run-in samples was 4. The acceptable standard of the reproducibility disclosed in a specific embodiment had RSD≤5% of an analysis result of four coal run-in samples.

The sub step 21 referred to using the EA equipment to analyze a substrate background of the Kit Blank, wherein the Kit Blank described above were put randomly in different positions during the batch analysis to determine the sulfur content, then the average integral area of the sulfur content was calculated.

The substep 22 referred to using the EA equipment to analyze a contrast substance, wherein five dealt coal standards as described above which had a weight selected from the range of 1 to 3.5 mg were ranked from low to high to determine the sulfur content in turn. After subtracting system background (i.e. the average background integral area) from the analytic area of sulfur content, coal standards were corresponded to the analytic area of the sulfur content to construct a calibration curve of linear regression and calculate the linear relation.

The substep 23 referred to using the EA equipment to analyze a QC sample, wherein the dealt QC sample described above was put randomly in different positions during batch analysis to determine sulfur content. After subtracting system background (i.e. the average background integral area) from the analytic area of sulfur content, the corresponding calibration curve of the sulfur content was calculated by the interpolation.

The substep 24 referred to using the EA equipment to analyze samples, wherein the dealt samples described above were put randomly in different positions during batch analysis to determine sulfur content. After subtracting the sulfur average background integral area of the blank sample substrate from the analytic area of sulfur content, the corresponding of the sulfur content was calculated by interpolation.

3.3 A Calculating Step for the Content of the Contrast Substance and the Quality Control Sample Proceeding to the step 3, which referred to a calculating step for the content of the contrast substance and the quality control sample, further comprised a calculating substep 30 for a linear regression formula and correlation coefficients of the contrast substance, and a calculating substep 31 for the accuracy and the recovery yield of the quality control sample, wherein the process 30 could be optionally before the process 31, or vice versa.

The substep 30 further comprised: a substep 300 for calculating the sulfur content of the contrast substance, wherein the sulfur content of the contrast substance (mg)=sample weight (mg)×sulfur content percentage of samples (%); a substep 301 for preparing a calibration curve, wherein the calibration curve was constructed by using the sulfur content of the contrast substance (mg) to correspond to the sulfur integral area (from which the average integral area of the system background was subtracted), and in certain embodiment the contrast substance was coal; a substep 302 for calculating a linear regression formula and correlation coefficients (r), wherein the linear regression formula: sulfur integral area=slope×sulfur content+intercept, in which the linear acceptable standard had a greater or equal 0.995 of a square of linear correlation coefficient ($r^2$).

Calculating an accuracy and a recovery yield of the quality control sample referred to a substep 31. The accuracy disclosed herein meant to an approximation between an experiment result and a theoretical value by the recovery yield. Calculating an experiment result of the sulfur content by a sulfur content percent of QC samples, followed by the ratio of the experiment result and the theoretical value of sulfur content. Generally, the batch test could be accurate according to the QC samples which should have a greater than 66.7% recovery yield. In one embodiment, QC samples had a recovery yield selected from the range of 95~105%.

The substep 310 referred to calculating a sulfur content theoretical value of the QC sample, wherein the sulfur content theoretical value of the QC sample=the weight of QC samples (mg)×sulfur content percent theoretical value of the QC sample (%).

The substep 311 referred to calculating a sulfur content experiment result of the QC sample, wherein the sulfur content experiment result of the QC sample=the weight of QC samples (mg)×sulfur content percent experiment result of the QC sample (%) and the substep 310 may be optionally before the substep 311, or vice versa.

The substep 312 referred to calculating a recovery yield, wherein the recovery yield (%)=the sulfur content experiment result of the QC sample (mg)/the sulfur content theoretical value of the QC sample (mg)×100%. The standard curve of coal contrasts and testing results of a precision and an accuracy of QC sample were shown in FIG. 4, in which testing results exhibited a correlation coefficient of 0.9989~0.9994 of samples and QC samples had a RSD of 0.6%~2.25%. Experiment results described above demonstrated that the method had a good precision and accuracy.

TABLE 4

The Standard Curve Of Coal Contrasts And Testing Results Of The Precision And The Accuracy Of QC Samples

| Sulfur weight (mg) | The linear regression formula | Correlation coefficient | Sulfur weight of QC samples (%) (Relative standard deviation %) | Recovery yield of the QC sample (%) |
|---|---|---|---|---|
| 0.033~0.104 | Y = 1.615 × $10^{-6}$X + 4.747 × $10^{-3}$ | 0.9993 | 3.13 ± 0.07 (2.25%) | 102.08 ± 2.29 |
| 0.031~0.105 | Y = 1.623 × $10^{-6}$X + 1.741 × $10^{-3}$ | 0.9989 | 3.10 ± 0.02 (0.60%) | 100.89 ± 0.60 |
| 0.034~0.107 | Y = 1.634 × $10^{-6}$X + 1.034 × $10^{-3}$ | 0.9994 | 3.08 ± 0.04 (1.21%) | 100.15 ± 1.21 |

3.4 The Converting Substep 4

The converting substep 4, which calculated the sulfur content of a sample into content of a sulfur-containing chelator, further comprised a substep 40 and a substep 41. The substep 40 referred to calculating a sulfur content in a testing substance, wherein the sulfur content in a testing substance (mg) =total weight of the testing substance (mg)×sulfur content percent experiment result of the testing substance (%); the substep 41 referred to calculating the chelator content in a testing substance, which the calculating formula were as follows, chelator content (mg)=(the sulfur content in a testing substance (mg))×molecular weight of chelator (g/mol))/(sulfur number in the chelator×molecular weight of sulfur (g/mol)). In a specific embodiment, the chelator was ECD.2HCl, wherein the content of ECD.2HCl was calculated following according to the formula as described above: ECD.2HCl (mg)×(the sulfur content in a testing substance (mg)×molecular weight of ECD.2HCl (g/mol))/(2×molecular weight of sulfur (g/mol)). FIG. 5 shows the analytic result of ECD.2HCL content determined by EA, wherein the coal contrast substance exhibited a correlation coefficient of 0.9989~0.9994 of a standard calibration curve, while QC samples had a recovery yield of 99.52~106.62. These results described above exhibited that the solid sample analytic method disclosed herein could exactly determine the weight of ECD.2HCl.

Additionally, experimental parameters could be adjusted in the solid sample analytic method disclosed herein to find out the range of these parameters. The robustness test of adjusting parameters were shown in FIG. 6, wherein the coal contrast substance had a correlation coefficient of a standard calibration curve greater than 0.9989~0.9994 and QC samples had a recovery yield of 97~404.94% when the injection time of O2 was within the range of 90 to 150 sec, the temperature of the combustion tube was at the range of 1120 to 1180° C., and the temperature of the reduction tube was at the range of 850 to 950° C.

TABLE 5 the analytic result of ECD•2HCL content determined by EA

| Experiment | Sulfur weight (mg) | The linear regression formula | Correlation coefficient | Recovery yield of the QC Sample (%) | Weight (mg) |
|---|---|---|---|---|---|
| 1 | 1.025~3.327 | Y = 1.624 × $10^{-6}$X + 1.600 × $10^{-3}$ | 0.9995 | 101.26 | 0.934 ± 0.021 |
| 2 | 1.058~3.403 | Y = 1.582 × $10^{-6}$X + 1.791 × $10^{-3}$ | 0.9994 | 100.81~101.94 | 0.952 ± 0.013 |
| 3 | 1.033~3.376 | Y = 1.629 × $10^{-6}$X + 7.410 × $10^{-4}$ | 0.9998 | 99.52~106.62 | 0.984 ± 0.007 |

TABLE 6

Robustness test of adjusting parameters

| Experimental parameters | | The linear regression formula | Correlation coefficient | Sulfur weight (%) | Recovery yield (%) |
|---|---|---|---|---|---|
| Injection time of $O^2$ | 90 | $Y = 1.544 \times 10^{-6}X + 3.394 \times 10^{-3}$ | 0.9992 | 3.14 ± 0.06 | 102.36 ± 2.58 |
| | 120 | $Y = 1.615 \times 10^{-6}X + 4.747 \times 10^{-3}$ | 0.9993 | 3.13 ± 0.07 | 101.91 ± 2.30 |
| | 150 | $Y = 1.604 \times 10^{-6}X + 7.508 \times 10^{-4}$ | 0.9999 | 3.05 ± 0.10 | 99.17 ± 2.84 |
| Temperature of the combustion tube (° C.) | 1120 | $Y = 1.605 \times 10^{-6}X + 8.215 \times 10^{-4}$ | 0.9997 | 3.13 ± 0.06 | 102.01 ± 1.85 |
| | 1150 | $Y = 1.615 \times 10^{-6}X + 4.747 \times 10^{-3}$ | 0.9993 | 3.13 ± 0.07 | 101.91 ± 2.30 |
| | 1180 | $Y = 1.586 \times 10^{-6}X + 1.126 \times 10^{-3}$ | 0.9985 | 3.03 ± 0.03 | 98.68 ± 1.14 |
| Temperature of the reduction tube (° C.) | 850 | $Y = 1.621 \times 10^{-6}X + 9.226 \times 10^{-5}$ | 0.9997 | 3.12 ± 0.06 | 102.01 ± 1.75 |
| | 900 | $Y = 1.615 \times 10^{-6}X + 4.747 \times 10^{-3}$ | 0.9993 | 3.13 ± 0.07 | 101.91 ± 2.30 |
| | 950 | $Y = 1.649 \times 10^{-6}X - 1.288 \times 10^{-3}$ | 0.9996 | 3.00 ± 0.02 | 97.97 ± 0.87 |

As embodied and broadly described herein, disclosure herein features a direct solid sample analytical method for determining a content and a uniformity thereof in a lyophilized kit of a sulfur-containing chelator. For example, an EA coupled with NDIR, a thermal conductivity detector or an isotope ratio mass spectrometer is applied but not limit to exactly and effectively analyze the sulfur content of the sulfur-containing chelator in the solid lyophilized kit in the present invention and the chelator was further converted by a weight percent formula.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

Although the present invention has been explained in relation to its preferred embodiment, it is to be understood that many other possible modifications and variations can be made without departing from the spirit and scope of the invention as hereinafter claimed.

What is claimed is:

1. A direct solid sample analytical method for determining a content and a uniformity thereof in a lyophilized kit of a sulfur-containing chelator with a stable complex capacity for radiotechnetium (Tc-99m) and radiorhenium (Re-186, Re-188), comprising:

a sample-preparing step, which comprises a contrast substance preparing process and a lyophilized testing substance preparing process, wherein the contrast substance preparing process comprises: preparing a contrast substance, a run-in sample, a calibration curve standard and a quality control sample, while the lyophilized testing substance preparing process comprises: preparing a kit blank of the lyophilized testing substance and a sample, wherein the sample is related to the sulfur-containing chelator;

An analyzing step using an elemental analyzing equipment, wherein the elemental analyzing equipment is used for the following substeps, comprising: a system suitability test, a substrate background analysis for the kit blank of the lyophilized testing substance, a contrast substance analysis, a quality control sample analysis and a sample analysis, wherein the system suitability test comprises: a system background test and a run-in sample test;

A calculating step for a content of a contrast substance and a quality control sample, which comprises: a calculating substep for a linear regression formula and a correlation coefficient of the contrast substance and a calculating substep for an accuracy and a recovery yield of the quality control sample, wherein the calculating substep for the linear regression formula and the correlation coefficient of the contrast substance comprises: calculating a sulfur content of the contrast substance, preparing a calibration curve, and calculating the linear regression formula and correlation coefficients, while the calculating substep for an accuracy and a recovery yield of the quality control sample comprises: calculating a theoretical value and an experimental value for the sulfur content of the quality control sample and the recovery yield thereof; and A converting substep for calculating a sulfur content of a sample into a content of a sulfur-containing chelator, wherein comprises: calculating the sulfur content in a testing substance and calculating a chelator content in the testing substance.

2. The method as claimed in claim 1, wherein the elemental analyzing equipment is the elemental analyzing equipment, which coupled with a non-dispersive infrared detector, a thermal conductivity detector or a mass spectrometer.

3. The method as claimed in claim 2, wherein the mass spectrometer that the elemental analyzing equipment coupled with is an isotope ratio mass spectrometer, an inductively coupled plasma mass spectrometry, a gas chromatograph mass spectrometry, a liquid chromatography mass spectrophotometer or a tandem mass spectrometry.

4. The method as claimed in claim 1, wherein the sulfur-containing chelator refers to a precursor of the sulfur-containing chelator which has a stable complex capacity for radiotechnetium (Tc-99m) and radiorhenium (Re-186, Re-188) and is applied to diagnostic or therapeutic radiopharmaceuticals after chelating with radiotechnetium and radiorhenium.

5. The method as claimed in claim 4, wherein the sulfur-containing chelator further comprises: thiolates, aminothiolates, dithiolates, dithioxalates, tridentate dithiolates, tridentate schiff bases, diaminedithiolates, mercaptoacetamides, mercaptoacetyltriglycine (mag3) derivatives, thioalkyl-dithiol-thio, thiourea, dithiocarbamate, azomethines, diaminedithiols or isothiocyanate.

6. The method as claimed in claim 1, wherein the contrast substance is a sulfur-containing compound or a sulfur-containing mixture.

7. The method as claimed in claim 6, wherein the sulfur-containing compound comprises: sulfanilic acid or 4-aminobenzene sulfonic acid.

8. The method as claimed in claim 6, wherein the sulfur-containing mixture comprises coal.

* * * * *